US010661047B2

(12) United States Patent
Sato (10) Patent No.: US 10,661,047 B2
(45) Date of Patent: May 26, 2020

(54) LIGHT-EMITTING APPARATUS

(71) Applicant: PANASONIC INTELLECTUAL PROPERTY MANAGEMENT CO., LTD., Osaka (JP)

(72) Inventor: Ayumu Sato, Niigata (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 340 days.

(21) Appl. No.: 15/815,850

(22) Filed: Nov. 17, 2017

(65) Prior Publication Data
US 2018/0147386 A1 May 31, 2018

(30) Foreign Application Priority Data

Nov. 29, 2016 (JP) .................... 2016-231883

(51) Int. Cl.
| | | |
|---|---|---|
| A61M 21/02 | (2006.01) | |
| H05B 45/20 | (2020.01) | |
| F21V 7/00 | (2006.01) | |
| F21Y 113/13 | (2016.01) | |
| F21Y 115/10 | (2016.01) | |
| A61M 21/00 | (2006.01) | |

(52) U.S. Cl.
CPC .......... *A61M 21/02* (2013.01); *F21V 7/0008* (2013.01); *H05B 45/20* (2020.01); *A61M 2021/0044* (2013.01); *A61M 2205/50* (2013.01); *F21Y 2113/13* (2016.08); *F21Y 2115/10* (2016.08)

(58) Field of Classification Search
CPC .......... A61M 2021/0044; A61M 21/02; A61M 2205/50
See application file for complete search history.

(56) References Cited

U.S. PATENT DOCUMENTS

| | | | |
|---|---|---|---|
| 6,720,743 B2 * | 4/2004 | Yano .................... | H05B 39/044 315/291 |
| 2007/0268234 A1 | 11/2007 | Wakabayashi et al. | |
| 2010/0060195 A1 | 3/2010 | Tsuboi et al. | |

(Continued)

FOREIGN PATENT DOCUMENTS

| | | |
|---|---|---|
| JP | 2005-063687 | 3/2005 |
| JP | 2006-204928 | 8/2006 |
| JP | 2006-231057 | 9/2006 |

(Continued)

*Primary Examiner* — Christine H Matthews
(74) *Attorney, Agent, or Firm* — Greenblum & Bernstein, P.L.C.

(57) ABSTRACT

A light-irradiating apparatus which emits light for activating a body is provided. The light-irradiating apparatus includes a blue light source, a white light source, and a controller. The controller controls the white light source and the blue light source, and adjusts irradiation intensities of light emitted by the blue light source and the white light source. The controller causes the white light source to continuously maintain an on state and causes the blue light source to repeat an on state and an off state. The controller causes a sum of the irradiation intensity of the light which is emitted by the white light source and the irradiation intensity of the light which is emitted by the blue light source to be greater than or equal to a biological effect threshold at which light produces an effect of activating the body.

15 Claims, 7 Drawing Sheets

(56) References Cited

U.S. PATENT DOCUMENTS

2010/0161010 A1\* 6/2010 Thomas ............... A61M 21/00
607/88

FOREIGN PATENT DOCUMENTS

| JP | 2007-299714 | 11/2007 |
|----|-------------|---------|
| JP | 2009-259639 | 11/2009 |
| JP | 2010-022672 | 2/2010 |
| JP | 2013-127853 | 6/2013 |
| WO | 2008/069103 | 6/2008 |

\* cited by examiner

FIG. 7

LIGHT-EMITTING APPARATUS

CROSS REFERENCE TO RELATED APPLICATION

This application claims the benefit of priority of Japanese Patent Application Number 2016-231883 filed on Nov. 29, 2016, the entire content of which is hereby incorporated by reference.

BACKGROUND

1. Technical Field

The present disclosure relates to a light-emitting apparatus which emits light for activating a body.

2. Description of the Related Art

Conventionally, a light-emitting apparatus which includes a first light emitter which emits blue light, a second light emitter which emits blue light having an emission peak wavelength different from the emission peak wavelength of the first light emitter, and a lighting control means which selectively turns on the first light emitter and the second light emitter is disclosed (for example, see Japanese Unexamined Patent Application Publication No. 2005-63687). Furthermore, Japanese Unexamined Patent Application Publication No. 2005-63687 discloses that the light-emitting apparatus emits white light using a combination of the first light emitter and the second light emitter, for instance.

The light-emitting apparatus has a function of adjusting a biological rhythm, and influences the biological rhythm at all times while the light-emitting apparatus is on, by using a light emitter which emits light having a wavelength of 445 nm to 480 nm as a blue light source.

SUMMARY

However, such a conventional light-emitting apparatus emits light which influences the biological rhythm at all times while a blue light source is on, and thus a user perceives the light as being glaringly bright. In view of this, the user is less likely to perceive light as being glaringly bright if the brightness of light emitted by the light-emitting apparatus is decreased. Yet, a decrease in the brightness of light results in a difficulty of giving influence to a biological rhythm. Accordingly, there has been a demand for a light-emitting apparatus which emits light which activates the body of a user, yet the user is less likely to perceive emitted light as being glaringly bright.

In view of this, the present disclosure is to provide a light-emitting apparatus which can emit light which activates the body of a user, yet the user is less likely to perceive emitted light as being glaringly bright.

In order to provide such a light-emitting apparatus, a light-emitting apparatus according to an aspect of the present disclosure is a light-emitting apparatus which emits light for activating a body, the light-emitting apparatus including: a blue light source; a white light source; and a controller which controls the white light source and the blue light source and which adjusts an irradiation intensity of light emitted by the blue light source and an irradiation intensity of light emitted by the white light source, wherein the controller causes the white light source to continuously maintain an on state and causes the blue light source to repeat an on state and an off state, and the controller causes a sum of the irradiation intensity of the light which is emitted by the white light source and the irradiation intensity of the light which is emitted by the blue light source to be greater than or equal to a biological effect threshold at which light produces an effect of activating the body.

According to the present disclosure, light that a user is less likely to perceive as being glaringly bright can be emitted while light which activates the body of the user is emitted.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENTS (Underlying Knowledge Forming Basis of the Present Disclosure)

It is generally known that a body is activated if light having a predetermined wavelength taken in through the eyes. Light which activates the body includes blue light and white light. With regard to blue light, it is known that exposure to light which includes blue light for a predetermined time period or longer is effective in improving a biological rhythm (circadian rhythm). In particular, the exposure to blue light in a period from the morning to around 3:00 p.m. is known to be effective in increasing the amount of generated biological hormone such as serotonin. Also, with regard to white light, it is known that the exposure to light which includes white light for a predetermined period or longer is effective in activating brain waves.

Accordingly, it is desirable to activate a body by simultaneously taking in blue light and white light through the eyes. Here, a biological rhythm is about a one day cycle in which as physiological phenomena, a person feels sleepy at a certain time and naturally wakes up after sleeping for a certain time period.

An increase in the amount of secreted serotonin caused by the exposure to light promotes generation of melatonin that affects a biological rhythm (biological clock). Melatonin is readily produced during night, which leads to good sleep.

With regard to sensitivity of the human eye, the human eye is known to mainly perceive light having a wavelength in a range from 380 nm to 780 nm. It is known that the human eye has highest sensitivity (also referred to as biological effect light sensitivity) to blue light having a wavelength in a range from 460 nm to 490 nm which most influences a biological rhythm of a person (in the present embodiment, the human eye has highest sensitivity to light having a wavelength of 480 nm). Accordingly, light emitted to the human eye desirably include a large amount of light having a wavelength in a range from 460 nm to 490 nm.

Exposure to such blue light for at least an hour and half, which is an accumulated time period, at about 1.75 $\mu W/cm^2$ which is a biological effect threshold (=biological effect light sensitivity×irradiance) is effective in activating the body. Specifically, the body can be activated by being exposed to blue light having a predetermined brightness for a predetermined time period, rather than just being exposed to blue light. The biological effect light sensitivity is a coefficient.

The above shows that it is desirable to efficiently expose the human eyes to light. However, when the light is exposed to the human eye, if light emitted by a light-emitting apparatus has high brightness, a person perceives the light as being glaringly bright. Thus, if a person perceives light as being glaringly bright, the person finds the light unpleasant, which reduces an incentive to be positively exposed to the light.

It is known that the human eye is most sensitive to light having a wavelength of 555 nm, and the sensitivity decreases as light is farther away from a wavelength of 555 nm. Accordingly, in view of the characteristics (relative luminous efficiency) of human eyes, it is considered that lowering the luminance at and around a wavelength of 555 nm is effective in preventing a person from perceiving the light as being glaringly bright.

Although lowering the brightness prevents a person from perceiving the light as being glaringly bright, light which is effective in activating the body cannot be emitted by simply lowering the brightness of the emitted light. Thus, there has been a demand for a light-emitting apparatus which emits light which activates the body of a user, yet the user is less likely to perceive emitted light as being glaringly bright.

The following describes embodiments of the present disclosure with reference to the drawings. The embodiments described below each illustrate a particular example of the present disclosure. Thus, the numerical values, shapes, materials, elements, the arrangement and connection of the elements, and others indicated in the following embodiments are mere examples, and are not intended to limit the present disclosure. Therefore, among the elements in the following embodiments, elements not recited in any of the independent claims defining the most generic part of the present disclosure are described as arbitrary elements.

In addition, the statement "approximately XX" is intended to mean, when using "approximately the same" as an example, not only completely the same, but also something that can be recognized as substantially the same.

Note that the drawings are schematic diagrams and do not necessarily give strict illustration. Throughout the drawings, the same numeral is given to approximately the same element, and redundant description is omitted or simplified.

The following describes a light-emitting apparatus according to embodiments of the present disclosure.

Embodiment

[Configuration]

Figure 1:
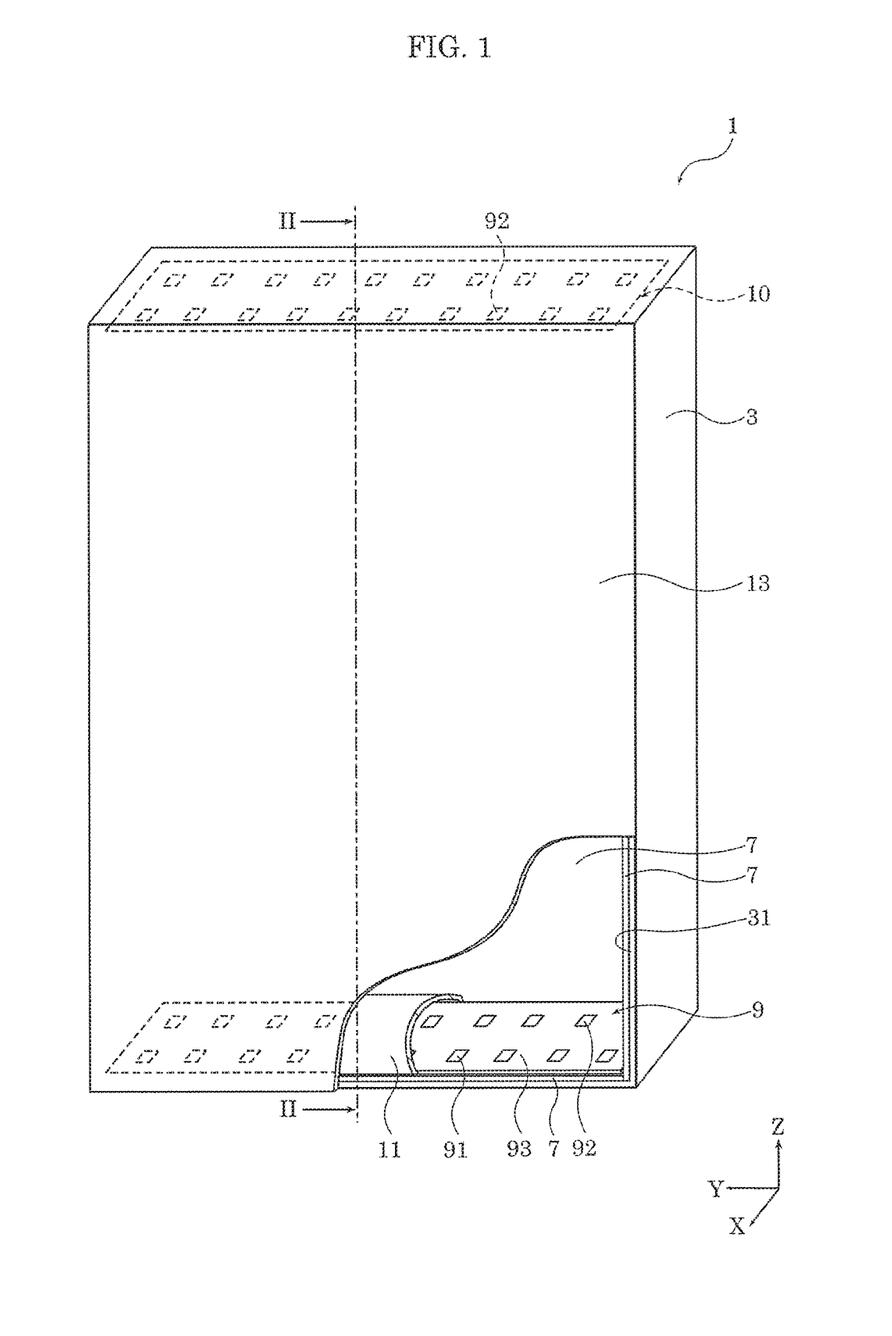
FIG. 1 is a perspective view illustrating a light-irradiating apparatus according to an embodiment.
Figure 2:
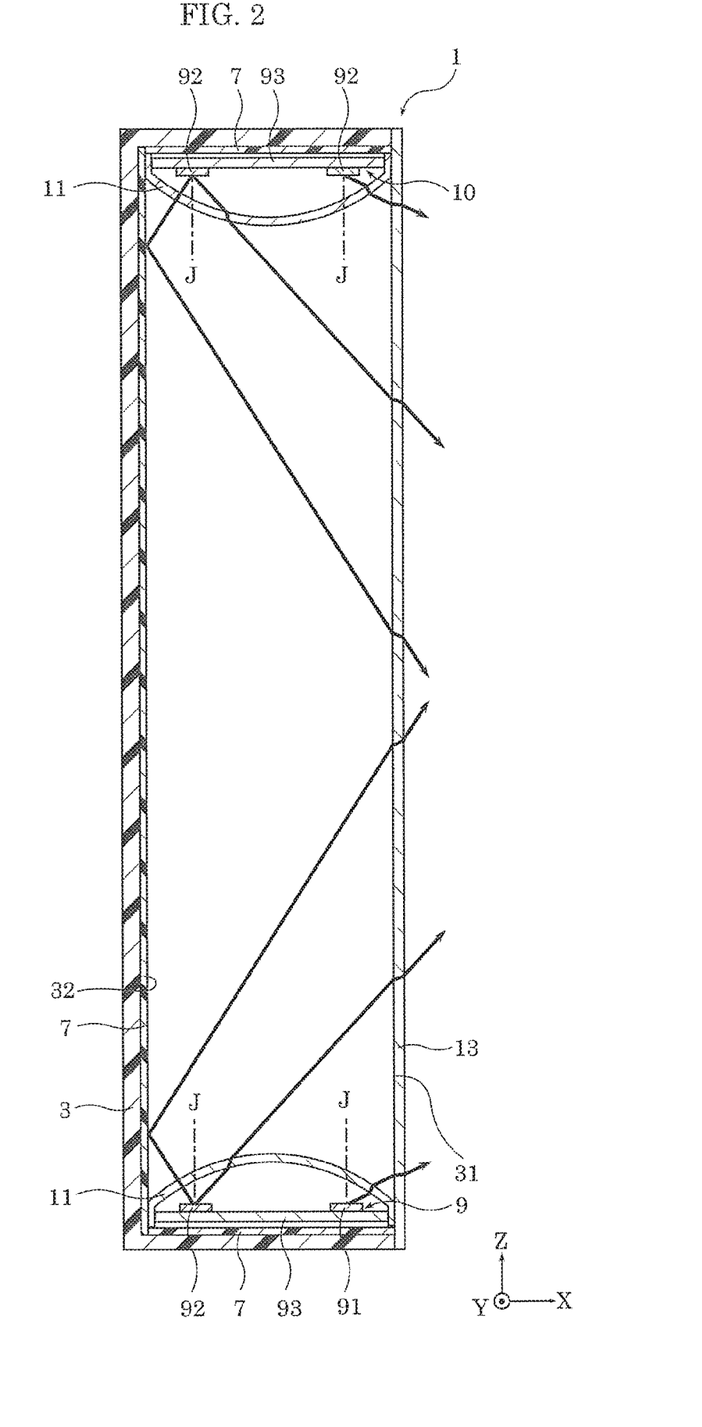
FIG. 2 is a cross-sectional view illustrating the light-irradiating apparatus according to the embodiment taken along line II-II in FIG. 1.
Figure 3:
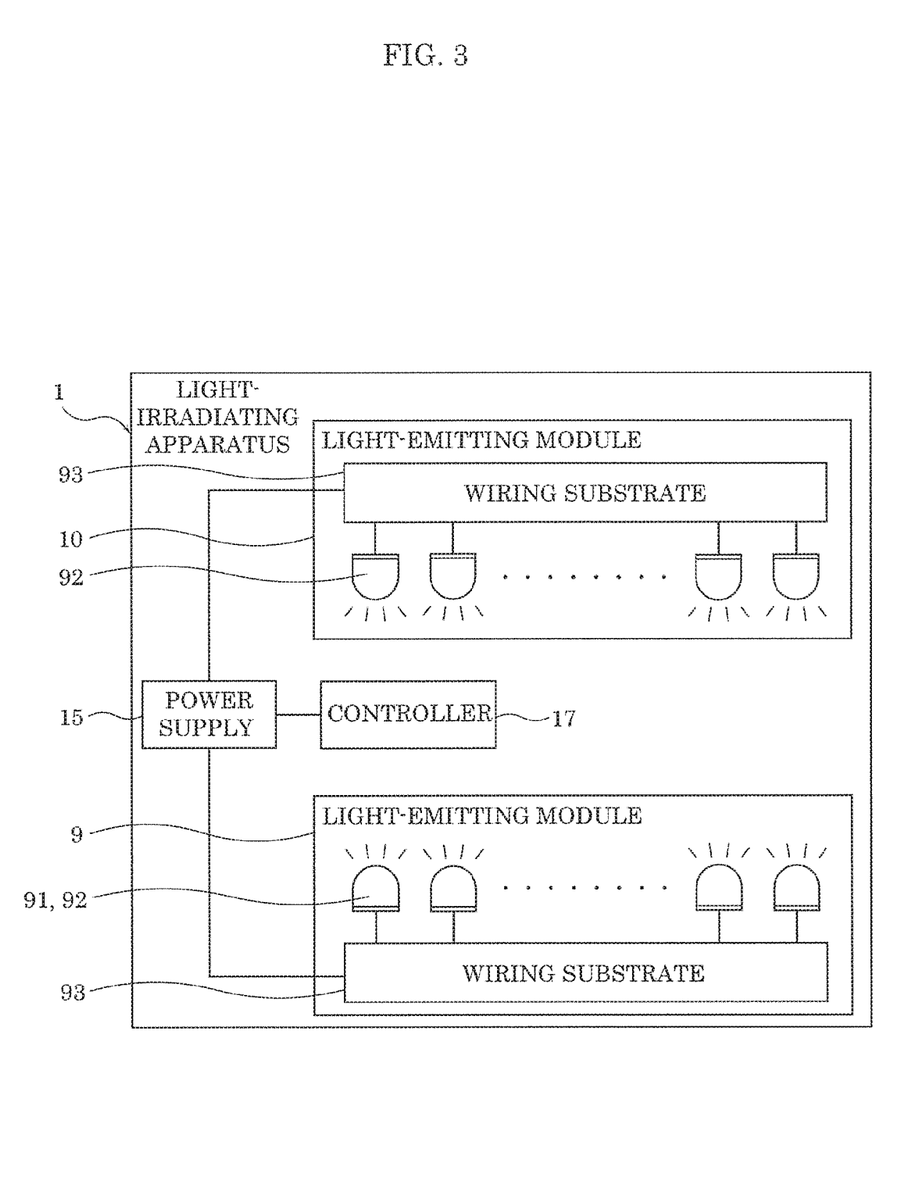
FIG. 3 is a block diagram illustrating the light-irradiating apparatus according to the embodiment.

The first describes a configuration of light-irradiating apparatus 1 according to the present embodiment with reference to FIGS. 3 to 1. The present embodiment gives a description using a light-irradiating apparatus as an example of a light-emitting apparatus.

FIG. 1 is a perspective view illustrating a light-irradiating apparatus according to the present embodiment. FIG. 2 is a cross-sectional view illustrating the light-irradiating apparatus according to the present embodiment taken along line II-II in FIG. 1. FIG. 3 is a block diagram illustrating the light-irradiating apparatus according to the present embodiment.

In FIG. 1, the transverse direction of light-irradiating apparatus 1 is defined as the Y axis direction, the longitudinal direction of light-irradiating apparatus 1 is defined as the Z axis direction, and the direction perpendicular to the Y axis direction and the Z axis direction is defined as the X axis direction. The directions illustrated in FIG. 2 and the subsequent diagrams all correspond to the directions illustrated in FIG. 1. Note that in FIG. 1, the X axis direction, the Y axis direction, and the Z axis direction may change depending on a used state, and thus the directions are not limited to those defined as above. The same applies to the subsequent diagrams. Note that in the present embodiment, the direction in which light-irradiating apparatus 1 emits light is defined as the positive direction of the X axis.

As illustrated in FIG. 1, light-irradiating apparatus 1 emits light which activate the body from the light-transmissive plate 13 side to a user. Light which activates the body is light which includes a large amount of blue light, and light obtained by adding white light to blue light, in the present embodiment. In the present embodiment, light-irradiating apparatus 1 can emit blue light and white light simultaneously. Light-irradiating apparatus 1 can be placed on, for example, a desk in an office, a dressing table, or the like so that a user can be exposed to light which activates the body of the user.

Note that blue light here does not mean light having a blue color in a strict sense, but rather means light that normally appears blue, an example of which is, for example, light having a wavelength in a range from 430 nm to 495 nm. White light here does not mean light having a white color in a strict sense, but rather means light that normally appears white, which is an approximately uniform mixture of visible light rays having different colors (such as, for example, blue light (430 nm to 495 nm), green light (495 nm to 570 nm), and red light (620 nm to 750 nm).

As illustrated in FIGS. 2 and 3, light-irradiating apparatus 1 has a flat rectangular box shape. Light-irradiating apparatus 1 includes casing 3, diffuser sheet 7, two light-emitting modules 9 and 10, controller 17, power supply 15, light-transmissive cover 11, and light-transmissive plate 13

Casing 3 is a box having a bottom flat in the X axis direction, and houses diffuser sheet 7, light-emitting modules 9 and 10, and power supply 15. Casing 3 in the present embodiment has a rectangular shape elongated in the Z axis direction in a plan view.

Casing 3 has opening 31 formed on the positive side of the X axis (front side). White diffuser sheet 7 which diffuses (reflects) light is disposed uniformly on the internal surface of casing 3. In the present embodiment, diffuser sheet 7 covers a rear surface (on the negative side of the X axis), a surface on the positive side of the Y axis, a surface on the negative side of the Y axis, a surface on the positive side of the Z axis, and a surface on the negative side of the Y axis inside of casing 3.

Diffuser sheet 7 is formed using, for example, a light-transmissive resin material such as an acrylic resin and a polycarbonate resin or a light-transmissive material such as a transparent glass material. In the present embodiment, diffuser sheet 7 has a function of diffusing light. For example, an opaque white light-diffusive film is formed on diffuser sheet 7 by causing a resin containing light-diffusive material (particles) such as silica or calcium carbonate or a white pigment to adhere to the internal surface or the external surface of diffuser sheet 7. Diffuser sheet 7 itself may be formed using, for instance, a resin material in which a light diffusing material is dispersed.

Diffuser sheet 7 may be configured to be given light diffusibility by being subjected to diffusion processing. For example, diffuser sheet 7 may be configured be given light diffusibility by forming fine unevenness in the surface of diffuser sheet 7 by being subjected to surface treatment such as texturing or by printing a dot pattern on the surface of a transparent cover.

Note that the material of diffuser sheet 7 is not limited to a light-transmissive material (transparent or translucent material). For example, a metal material such as aluminum or a hard white resin material (opaque resin) may be used for diffuser sheet 7. Specifically, diffuser sheet 7 may have a function of diffusing (reflecting) incident light.

Light-emitting modules 9 and 10 each include a plurality of light sources (white light sources 91 and blue light sources 92 later described), and wiring substrates 93 on which the plurality of light sources are disposed, and each have a plate shape elongated in the Y axis direction. The plurality of light sources are mounted on wiring substrates 93, in alignment with one another in the Y axis direction. In the present embodiment, light-emitting modules 9 and 10 are disposed on the surface on the negative side of the Z axis and the surface on the positive side of the Z axis inside of casing 3, respectively.

The light sources are light emitting diode (LED) elements of so-called surface mount device (SMD) type. Each of the SMD LED elements is, specifically, a packaged LED element in which an LED chip (light emitting element) is mounted in a resin-molded cavity and a phosphor-containing resin is enclosed in the cavity.

The light sources are controlled by controller 17 included in light-irradiating apparatus 1 so that the light sources emit light (intermittently emit light) such that on and off are repeated. Controller 17 controls dimming and the color of the light sources by controlling power supply 15 (adjusting the amount of power supplied). In the present embodiment, light-emitting modules 9 and 10 may be dimmable (brightness controllable) and color controllable (color of emitted light can be controlled). Controller 17 is achieved by, for instance, a microcomputer, a processor, or a dedicated circuit which controls a value of a current to be supplied to light-emitting modules 9 and 10, according to an input signal.

The light sources are disposed at equal intervals along the length direction (Y axis direction) of wiring substrates 93, in lines in the X axis direction. In the present embodiment, two lines of light sources are disposed on each wiring substrate 93 in the X axis direction.

In the present embodiment, first light-emitting module 9 (on the positive side of the Z axis) and second light-emitting module 10 (on the negative side of the Z axis) are approximately orthogonal to opening 31, and disposed in casing 3 such that light-emitting modules 9 and 10 emit light toward each other.

First light-emitting module 9 includes white light sources 91 and blue light sources 92. A line of light sources disposed in the Y axis direction on the positive side of the X axis in first light-emitting module 9 disposed in casing 3 are white light sources 91 which emit white light. Stated differently, white light sources 91 are disposed closer to opening 31 than blue light sources 92. A line of light sources disposed in the Y axis direction farther away from opening 31 than white light sources 91 are (on the negative side of the X axis relative to white light sources 91) in first light-emitting module 9 are blue light sources 92 which emit blue light. Stated differently, blue light sources 92 are disposed closer to the rear portion of casing 3 than white light sources 91, the rear portion being opposite opening 31.

In the present embodiment, white light sources 91 and blue light sources 92 are disposed on wiring substrates 93 so that optical axes J of the light sources are parallel to one another. White light sources 91 each emit light having a color temperature in a range from 2000 K to 8000 K. In the present embodiment, the color temperature of white light sources 91 is about 3000 K. If the color temperature of light from white light sources 91 is in a range from 2000 K to 8000 K, general-purpose light sources can be employed, and thus the manufacturing cost can be kept low.

On the other hand, second light-emitting module 10 includes blue light sources 92. In second light-emitting module 10 disposed in casing 3, light sources disposed in the Y axis direction in two lines on the positive side of the X axis are blue light sources 92 which emit blue light. In the present embodiment, blue light sources 92 are disposed on wiring substrate 93 such that optical axes J of blue light sources 92 are parallel to one another.

Note that in the present embodiment, light-emitting modules 9 and 10 are disposed such that optical axes J of the light sources included in light-emitting module 9 are approximately parallel to optical axes J of the light sources included in light-emitting module 10, but may not be approximately parallel. Stated differently, light-emitting modules 9 and 10 may be each disposed in an inclined state.

Controller 17 controls irradiation intensities (dimming) of light emitted by blue light sources 92 and white light source 91, in accordance with an indication from an operation unit. In other words, controller 17 controls the irradiation intensities of light emitted by light-emitting modules 9 and 10, based on an indication received from the operation unit through a signal line. For example, controller 17 outputs pulse width modulation (PWM) signals to light-emitting modules 9 and 10, and controls the irradiation intensities of light-emitting modules 9 and 10 by changing the duty cycles indicated by the PWM signals. This controls the irradiation intensity of light emitted by light-irradiating apparatus 1.

In the present embodiment, controller 17 performs PWM dimming, in which the duty cycle indicated by a PWM signal is changed, on blue light sources 92 of light-emitting modules 9 and 10 while white light sources 91 of first light-emitting module 9 are caused to continuously maintain the on state. Specifically, controller 17 controls blue light sources 92 to repeatedly turn on and off blue light sources 92. PWM dimming is for controlling the brightness of light from blue light sources 92, in accordance with a PWM signal transmitted from controller 17. Note that PWM dimming may be performed on blue light sources 92 of one of light-emitting modules 9 and 10. PWM dimming on blue light sources 92 is performed using a diode or a coil, for instance, without using a smoothing capacitor of a drive circuit.

Controller 17 sets a frequency (PWM frequency) at which blue light sources 92 repeats an on state and an off state to 500 Hz. This is because Japanese Industrial Standards stipulate that "light output should not give flicker to people", and one of the provisions requires that a condition "the repeat frequency of light output is 500 Hz or higher" be satisfied. In the present embodiment, controller 17 performs PWM dimming on blue light sources 92 at a PWM frequency of about 1 kHz.

Controller 17 calculates a second irradiation time by dividing a duty cycle of blue light sources 92 by a first irradiation time for activating the body. Controller 17 causes blue light sources 92 and white light sources 91 to emit light for the calculated second irradiation time, by controlling the light sources. Specifically, when a biological effect threshold is about 1.75 $\mu W/cm^2$, a user needs to be irradiated with light for 1.5 hours, and thus, for example, if the duty cycle is 50%, controller 17 divides 1.5 by 0.5 to calculate the second irradiation time, that is, three hours. For example, controller 17 causes blue light sources 92 and white light sources 91 to emit light for 3 hours with the biological effect threshold being about 1.75 $\mu W/cm^2$, by controlling the light sources. Note that 1.5 hours with the biological effect threshold being about 1.75 $\mu W/cm^2$ is an example of the first irradiation time, and the calculated three hours is an example of the second irradiation time, and thus the present disclosure is not limited to these numerical values.

In the present embodiment, controller 17 sets the duty cycle of blue light sources 92 in the on state (on duty) among the on state and the off state repeated to a value in a range from 20% to 75%. If the duty cycle is higher than 75%, light-irradiating apparatus 1 emits strongly bluish light, although a light irradiation time for activating the body can be decreased. Thus, a user will feel odd when the duty cycle is higher than 75%. On the other hand, if the duty cycle is lower than 20%, the strength of bluishness is lowered, yet a light irradiation time for activating the body is increased. For example, if the duty cycle is 10%, the accumulated light irradiation time needs to be 12 hours, and thus even if a user wakes up at 6:00 a.m., the user cannot secure a 12-hour light irradiation time by 3:00 p.m.

Figure 4:
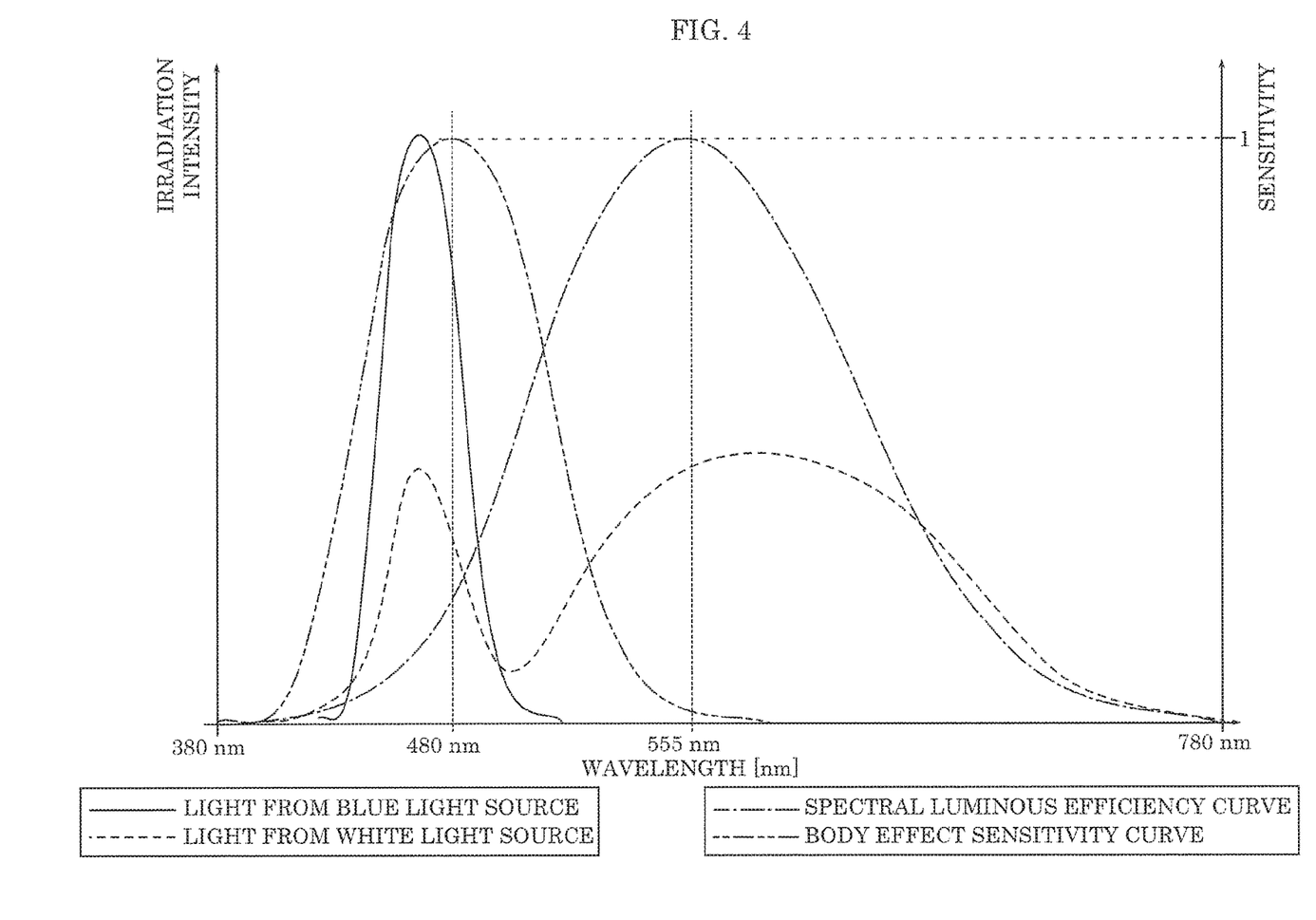
FIG. 4 is a diagram illustrating a spectrum of light from a white light source, a spectrum of light from a blue light source, a spectral luminous efficiency curve, and a body effect sensitivity curve, according to the light-irradiating apparatus according to the embodiment.
Figure 5:
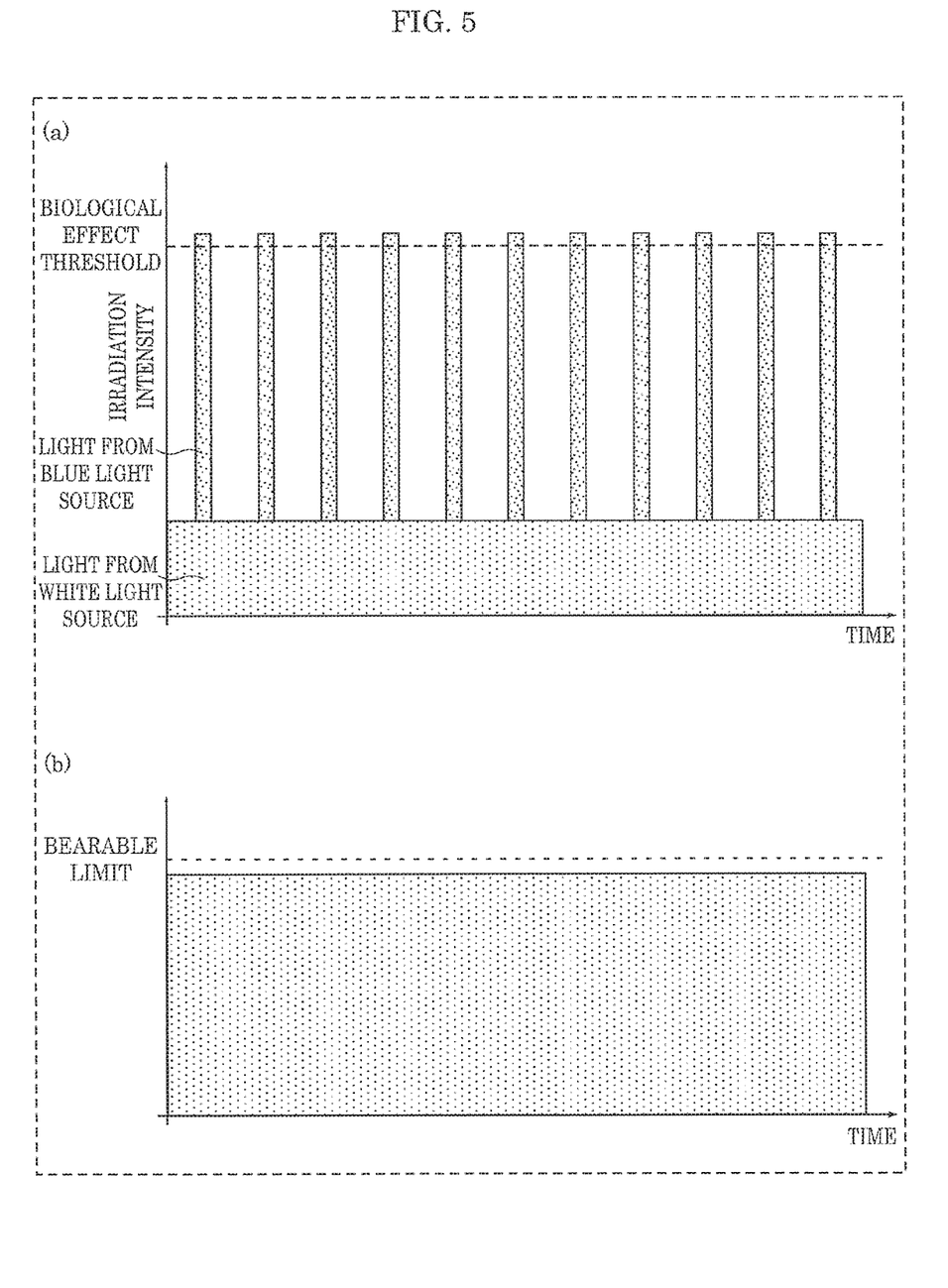
FIG. 5 is a diagram in which (a) illustrates a relation between a time during which blue light is emitted and an irradiation intensity at which blue light is emitted, according to the light-irradiating apparatus according to the embodiment, and (b) illustrates perceptual sensitivity according to the light-irradiating apparatus according to an embodiment.

FIG. 4 is a diagram illustrating a spectrum of light from a white light source, a spectrum of light from a blue light source, a spectral luminous efficiency curve, and a body effect sensitivity curve, according to light-irradiating apparatus 1 according to the present embodiment. Part (a) of FIG. 5 is a diagram illustrating a relation between a time during which blue light is emitted and an irradiation intensity at which blue light is emitted, according to light-irradiating apparatus 1 according to the present embodiment. Part (b) of FIG. 5 is a diagram illustrating perceptual sensitivity, according to light-irradiating apparatus 1 according to the present embodiment.

FIG. 4 illustrates light from blue light source 92 with the solid line, and light from white light source 91 with the dashed line, based on the relation between a wavelength and an irradiation intensity of light. Furthermore, FIG. 4 illustrates a spectral luminous efficiency curve with the dashed dotted line, and a body effect sensitivity curve with the two-dot chain line, based on the relation between a wavelength and sensitivity.

The spectral luminous efficiency is spectral luminous efficiency for photopic vision determined by the International Commission on Illumination (CIE) as an international standard, and expresses the ratio of visibility (relative sensitivity) with respect to a wavelength of light having the same strength when brightness perceived from light having a wavelength of 555 nm is set to 1. The body effect sensitivity expresses a ratio (relative sensitivity) of sensitivity to a wavelength of light having the same strength when a wavelength of light most suitable for activating the body (giving greatest influence to the biological rhythm of a person) is set to 1 with respect to light having a wavelength of 480 nm.

As illustrated in FIG. 4 and (a) of FIG. 5, controller 17 causes light-irradiating apparatus 1 to emit light whish has a value greater than or equal to a biological effect threshold and produces an effect of activating the body, by controlling light-irradiating apparatus 1. Specifically, controller 17 causes light-irradiating apparatus 1 to emit light such that light from blue light sources 92 and light which is included in light from white light source 91 and activates the body has a value greater than or equal to the biological effect threshold at which light produces an effect of activating the body, by controlling power supply 15. Here, the biological effect threshold is a threshold at which exposure to light having a predetermined brightness for a predetermined time period starts to actively secrete a sleep hormone called melatonin from the inside of the body. In the present embodiment, the biological effect threshold of light emitted from light-irradiating apparatus 1 is greater than or equal to about 1.75 $\mu W/cm^2$. Specifically, if the biological effect threshold is lower than 1.75 $\mu W/cm^2$, it is difficult to achieve an effect of activating the body.

Controller 17 causes light-emitting modules 9 and 10 to emit light such that a sum of an irradiation intensity of light which is included in light from white light sources 91 and activates the body and an irradiation intensity of light which is included in light from blue light sources 92 and activates the body is greater than or equal to the biological effect threshold at which light produces an effect of activating the body, by controlling the light-emitting modules. Specifically, a sum total $\int (V_S(\varepsilon)\Phi_W(\varepsilon)+V_S(\varepsilon)\Phi_B(\varepsilon))d\varepsilon$ is greater than or equal to the biological effect intensity, the sum total being a sum of a value (an example of the irradiation intensity of light which is included in light from white light sources 91 and activates the body) obtained by multiplying spectrum distribution $\Phi_W(\varepsilon)$ of light from white light sources 91 corresponding to $V_S(\varepsilon)$ by body effect sensitivity curve $V_S(\varepsilon)$, and a value (an example of the irradiation intensity of light which is included in light from blue light sources 92 and activates the body) obtained by multiplying spectrum distribution $\Phi_B(\varepsilon)$ of light from blue light sources 92 corresponding to $V_S(\varepsilon)$ by body effect sensitivity curve $V_S(\varepsilon)$, if sensitivity $V(\varepsilon)$ at the peak value of the body effect sensitivity curve is 1 in one on-off cycle of blue light sources 92. In other words, the sum total is a sum of an integral of a relative value, which expresses body effect sensitivity curve $V_S(\varepsilon)$ using spectrum distribution $\Phi_W(\varepsilon)$ and an integral of a relative value, which expresses body effect sensitivity curve $V_S(\varepsilon)$ using spectrum distribution $\Phi_B(\varepsilon)$.

As illustrated in (b) of FIG. 5, controller 17 changes the brightness of light from light-irradiating apparatus 1 by changing the duty cycle of blue light sources 92 involved in PWM dimming. Specifically, controller 17 causes light-irradiating apparatus 1 to emit light such that a sum of an average luminance of the light emission surfaces of blue light sources 92 per unit time with an average luminance of the light emission surfaces of white light sources 91 per unit time is less than or equal to a predetermined luminance. Note that in the present embodiment, light-irradiating apparatus 1 includes light-transmissive plate 13, and thus an average luminance of light emitted through the light exit surface of light-irradiating apparatus 1 may be used for the control, rather than the light emission surfaces of white light sources 91 and the light emission surfaces of blue light sources 92.

More specifically, controller 17 controls blue light sources 92 such that sum total $\int(V_S(\lambda)\Phi_B(\lambda)+V_S(\lambda)\Phi_W(\lambda))d\lambda$ is less than or equal to a predetermined luminance, the sum total being a sum of a value obtained by multiplying spectrum distribution $\Phi_B(\lambda)$ of light from blue light sources 92 corresponding to $V_S(\lambda)$ by sensitivity $V_S(\lambda)$ depending on the spectral luminous efficiency curve, and a value obtained by multiplying spectrum distribution $\Phi_W(\lambda)$ of light from white light sources 91 corresponding to $V_S(\lambda)$ by sensitivity $V_S(\lambda)$ depending on the spectral luminous efficiency curve, if sensitivity $V_S(\lambda)$ at the peak value of the spectral luminous efficiency curve is 1 in one on-off cycle of blue light sources 92. The predetermined luminance here is determined based on perceptual sensitivity indicating a bearable limit above which people perceive light as being glaringly bright. The perceptual sensitivity is a bearable limit which is derived from subjective evaluation and above which a person perceives light as being glaringly bright. If the brightness of light exceeds the perceptual sensitivity, a person perceives the light as being glaringly bright, whereas if the brightness of light is less than or equal to the perceptual sensitivity, a person is less likely to perceive the light as being glaringly bright.

In the present embodiment, the perceptual sensitivity was derived based on subjective evaluations as below. A square light emitter was placed in a position 30 cm ahead of a subject, and the area of the light emitter and an illuminance on the face of the subject were parameterized. Then, subjective evaluation of glaring brightness was conducted. The result was obtained, showing that when the average luminance of the light emitter was less than 20000 cd/m$^2$, the brightness was bearable for about 80% of subjects. Thus, the perceptual sensitivity was set to the numerical value.

Controller 17 controls the brightness of light from white light sources 91, and the duty cycle of blue light sources 92. For example, in order to activate the body by using only white light sources 91, the brightness (illuminance) of light from white light sources 91 is to be set to 3000 lx or higher. However, if blue light is added to white light, even if the brightness (illuminance) of light from light-irradiating apparatus 1 is reduced down to 1500 lx, an effect of activating the body can be acquired. Specifically, if the on-duty of blue light sources 92 is increased, the brightness of light from blue light sources 92 increases. Thus, controller 17 lowers the brightness of light from white light sources 91. If the on-duty of blue light sources 92 is decreased, the brightness of light from blue light sources 92 falls, and thus controller 17 increases the brightness of light from white light sources 91. Note that in (a) of FIG. 5, light emitted by white light sources 91 and light emitted by blue light sources 92 both have constant intensities, which is a mere example. The irradiation intensity of blue light included in light emitted by white light sources 91 and the irradiation intensity of blue light emitted by blue light sources 92 may not be constant.

Furthermore, 1500 lx which indicates the brightness (illuminance) of light from light-irradiating apparatus 1 is an example. For example, if the color temperature of light from white light sources 91 is 5000 K and the biological effect threshold is about 1.75 μW/cm$^2$, the brightness (illuminance) of light from light-irradiating apparatus 1 may be greater than or equal to about 750 lx, or more preferably greater than or equal to 1500 lx.

Power supply 15 includes a power supply circuit which generates power for causing light-emitting modules 9 and 10 to emit light. Power supply 15 converts power supplied from, for example, an electric power system into predetermined-level DC power by rectifying the power or decreasing the voltage of the power, for instance. Then, power supply 15 supplies the DC power to light-emitting modules 9 and 10. Power supply 15 is electrically connected with the electric power system by a power line such as a control line.

Power supply 15 is controlled by controller 17 so that power supply 15 allows and stops power supply to light-emitting modules 9 and 10. For example, when turn-on operation is received via an operation unit such as a remote control, controller 17 supplies power from power supply 15 to light-emitting modules 9 and 10 to turn on light-emitting modules 9 and 10. When the operation unit receives turn-off operation, controller 17 intercepts power supply from power supply 15 to turn off light-emitting modules 9 and 10.

Note that in light-irradiating apparatus 1, single power supply 15 may be used to turn on white light sources 91 and blue light sources 92 or two power supplies 15 may be used to turn on white light sources 91 and blue light sources 92, one of which is for turning on white light sources 91 and the other of which is for turning on blue light sources 92. If two power supplies 15 may be used to turn on white light sources 91 and blue light sources 92, operation on the operation unit connected to power supplies 15 controls dimming and the color of light.

Light-transmissive cover 11 is fixed to casing 3, covering light-emitting modules 9 and 10. In the present embodiment, two light-transmissive covers 11 cover light-emitting modules 9 and 10, separately. Light-transmissive covers 11 are light-transmissive members elongated in the Y axis direction, and each curve in an arc form in a cross section defined by the X and Z axis directions.

Two light-transmissive covers 11 may be formed using the same material as that of diffuser sheet 7, may have a function of diffusing light similarly to that of diffuser sheet 7, and may be subjected to diffusion processing to be given the same light diffusibility as diffuser sheet 7.

Light-transmissive plate 13 is a flat plate which transmits light, and has a rectangular shape having a size equivalent to the size of opening 31 of casing 3. Light-transmissive plate 13 is fixed to the edges of casing 3 on the positive side of the X axis, covering opening 31 of casing 3. Light-transmissive plate 13 has a function of diffusing light emitted from white light sources 91 and blue light sources 92. Light-transmissive plate 13 may also be formed using the same material as that of diffuser sheet 7, may have a function of diffusing light similarly to that of diffuser sheet 7, and may be subjected to diffusion processing which gives the same light diffusibility as that of diffuser sheet 7.

Figure 6:
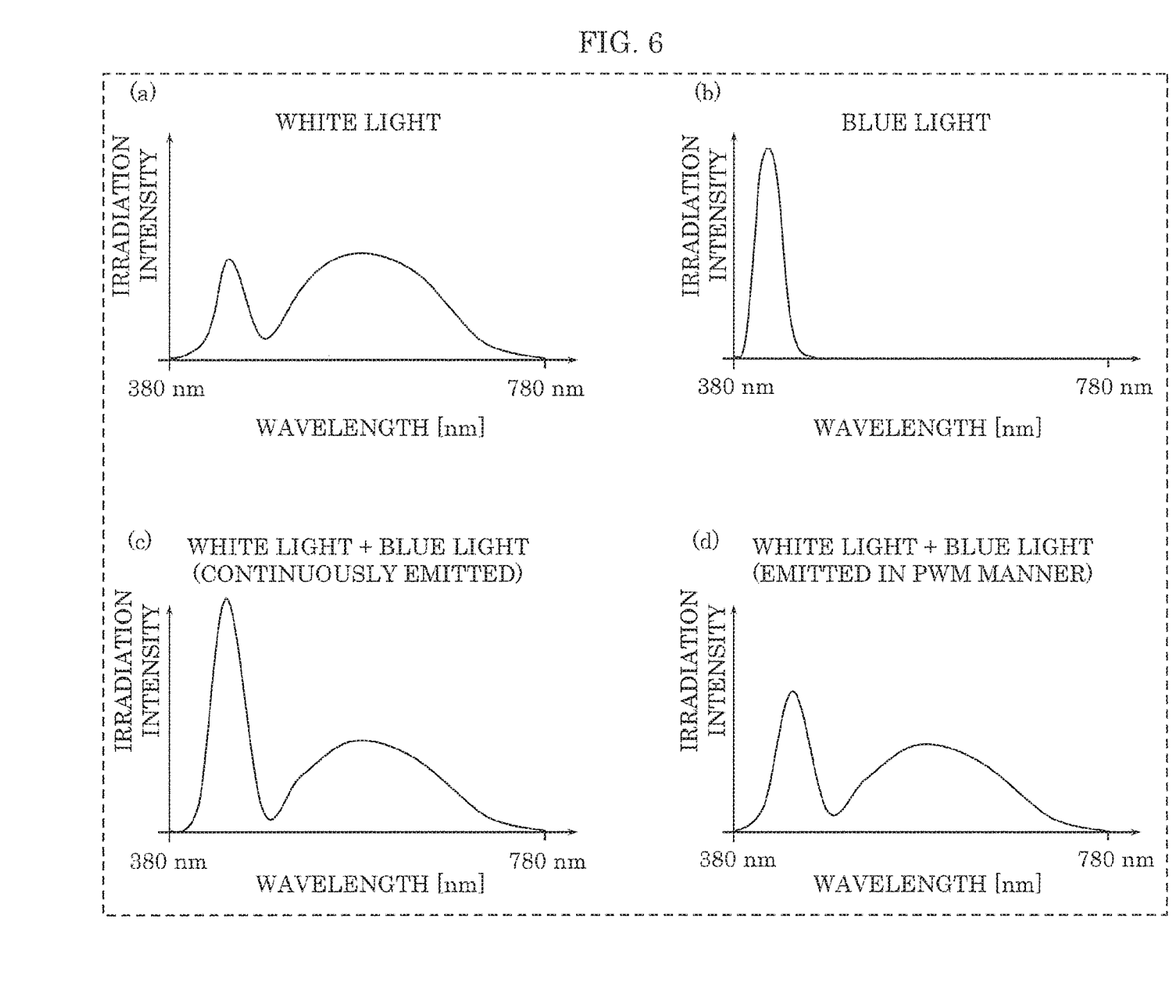
FIG. 6 includes spectrum diagrams in which (a) illustrates a relation between a wavelength and an irradiation intensity of white light from white light source 91, (b) illustrates a relation between a wavelength and an irradiation intensity of blue light from blue light source 92, (c) illustrates a relation between a wavelength and an irradiation intensity of continuously emitted blue light and continuously emitted white light, and (d) illustrates a relation between a wavelength and an irradiation intensity of continuously emitted white light and blue light emitted in a pulse width modulated (PWM) manner.

Next, a spectrum of light emitted from light-irradiating apparatus 1 is described.

Part (a) of FIG. 6 is a spectrum diagram illustrating a relation between a wavelength and an irradiation intensity of white light from white light sources 91. Part (b) of FIG. 6 is a spectrum diagram illustrating a relation between a wavelength and an irradiation intensity of blue light from blue light sources 92. Part (c) of FIG. 6 is a spectrum diagram illustrating a relation between a wavelength and an irradiation intensity of white light and blue light continuously emitted. Part (d) of FIG. 6 is a spectrum diagram illustrating a relation between a wavelength and an irradiation intensity of white light continuously emitted and blue light emitted in a PWM manner.

Specifically, if only white light sources 91 of light-irradiating apparatus 1 are continuously on, light appears as illustrated in (a) of FIG. 6. If only blue light sources 92 of light-irradiating apparatus 1 are continuously on, light appears as illustrated in (b) of FIG. 6. If light sources 91 and blue light sources 92 of light-irradiating apparatus 1 are all continuously on, light appears as illustrated in (c) of FIG. 6. If light sources 91 of light-irradiating apparatus 1 are continuously on and blue light sources 92 are on in the PWM manner, light appears as illustrated in (d) of FIG. 6.

A user perceives light as illustrated in (d) of FIG. 6, yet in fact, the state as illustrated in (a) of FIG. 6 and the state as illustrated in (c) of FIG. 6 alternately appear.

Figure 7:
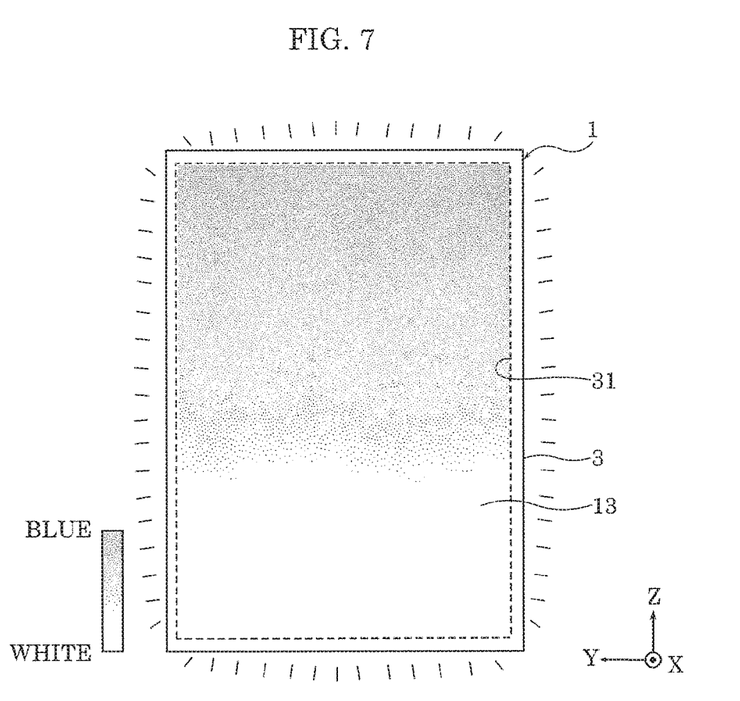
FIG. 7 is an explanatory diagram illustrating light emitted from the light-irradiating apparatus according to the embodiment.

FIG. 7 is an explanatory diagram illustrating light emitted by light-irradiating apparatus 1 according to the present embodiment.

According to light-irradiating apparatus 1 having such a configuration, as illustrated in FIG. 7, when white light sources 91 and blue light sources 92 of light-emitting modules 9 and 10 are turned on, one side of light-irradiating apparatus 1 on which light-emitting module 9 is disposed appears white, and the other side of light-irradiating apparatus 1 on which light-emitting module 10 is disposed appears blue. Specifically, the color gradually changes from white to blue like gradations from one side of light-transmissive plate 13 to the other side thereof (in the present embodiment, from the negative side of the Z axis to the positive side of the Z axis).

Light-irradiating apparatus 1 intermittently emits blue light, so as to emit light as a result of superimposing blue light on white light. Accordingly, compared to the case where white light sources 91 and blue light sources 92 are continuously on, the brightness of light emitted from light-irradiating apparatus 1 can be made not too high.

When a user is irradiated with light using light-irradiating apparatus 1, light-irradiating apparatus 1 is placed away from the user by a predetermined distance, and emits blue light and white light. In this manner, the user is exposed to blue light and white light emitted by light-irradiating apparatus 1 simultaneously. If the user is exposed to light having a predetermined brightness for a predetermined time period, a sleep hormone called melatonin is actively secreted from the inside of the body. The user can expect to have his/her body activated by being exposed to light every day using light-irradiating apparatus 1.

Advantageous Effects

The following describes advantageous effects produced by light-irradiating apparatus 1 according to the present embodiment.

As described above, light which activates the body is included in light from light-irradiating apparatus 1 according to the present embodiment. Light-irradiating apparatus 1 includes blue light sources 92, white light sources 91, and controller 17 which controls white light sources 91 and blue light sources 92 and which adjusts irradiation intensities of light emitted by blue light sources 92 and white light sources 91. Controller 17 causes white light sources 91 to continuously maintain an on state, and causes blue light sources 92 to repeat an on state and an off state. Controller 17 causes a sum of the irradiation intensity of light which is emitted by white light sources 91 and the irradiation intensity of light which is emitted by blue light sources 92 to be greater than or equal to the biological effect threshold at which light produces an effect of activating the body.

According to this, white light sources 91 are continuously on, and blue light sources 92 repeats on and off, and thus the brightness of light emitted by light-irradiating apparatus 1 is lower than that in the case where white light sources 91 and blue light sources 92 are continuously on. Accordingly, compared with the case where the light sources are continuously on, a user is less likely to perceive the light as being glaringly bright.

Light having the biological effect threshold or higher at which light produces an effect of activating the body is emitted even though the brightness of light lowers, and thus an influence can be given to the biological rhythm.

Accordingly, light-irradiating apparatus 1 can emit light which activates the body of a user, yet the user is less likely to perceive emitted light as being glaringly bright.

As described above, in light-irradiating apparatus 1 according to the present embodiment, the duty cycle of blue light sources 92 in the on state among the on state and the off state repeated is in a range from 20% to 75%.

According to this, the duty cycle of blue light sources 92 is greater than or equal to 20%, and thus a light irradiation time can be secured in a time period from the morning to 3:00 p.m. For example, if the duty cycle of blue light sources 92 is 20%, even if a user wakes up at 7:00 a.m., the user can secure a light irradiation time by 3:00 p.m.

The duty cycle of blue light sources 92 is 75% or less, and thus compared to when the duty cycle is 100%, a user is less likely to appear bluish, which prevents others who look at the user from feeling odd. Accordingly, light-irradiating apparatus 1 can provide an optimal light irradiation environment since the duty cycle of blue light sources 92 is in an optimal range.

As described above, in light-irradiating apparatus 1 according to the present embodiment, a frequency at which blue light sources 92 repeat on and off is greater than or equal to 500 Hz.

According to this, the frequency prevents a user from feeling flickers, and thus the user is less likely to feel unpleasant through the use of light-irradiating apparatus 1.

As described above, in light-irradiating apparatus 1 according to the present embodiment, a sum of an average luminance of the light emission surfaces of blue light sources 92 and the average luminance of the light emission surfaces of white light sources 91 is less than or equal to the predetermined luminance.

According to this, a sum of the average luminances is equal to or less than the predetermined luminance, and thus the user is less likely to perceive the light emitted by light-irradiating apparatus 1 as being glaringly bright.

As described above, the brightness of light emitted by light-irradiating apparatus 1 according to the present embodiment may be greater than or equal to 750 lx. Furthermore, as described above, the brightness of light emitted by light-irradiating apparatus 1 according to the present embodiment may be greater than or equal to 1500 lx.

According to these, for example, rather than setting the brightness of light from white light sources 91 to 3000 lx or higher in order to activate the body by using only white light sources 91, an effect of activating the body can be acquired by simply adding intermittent blue light to white light, even if the brightness of light from light-irradiating apparatus 1 is reduced to a range from about 750 lx to about 1500 lx. Accordingly, the brightness can be made lower than the brightness in the case where only white light sources 91 emit light. Accordingly, a user is less likely to perceive light as being glaringly bright.

As described above, in light-irradiating apparatus 1 according to the present embodiment, controller 17 divides the duty cycle of blue light sources 92 by a first irradiation time for activating the body to calculate a second irradiation time. Controller 17 causes blue light sources 92 and white light sources 91 to emit light for the second irradiation time by controlling the light sources.

According to this, controller 17 causes emission of light having a predetermined brightness to a user for an appropriate irradiation time period, and thus can activate the body of the user.

In particular, even if a user changes the duty cycle while using light-irradiating apparatus 1, light-irradiating apparatus 1 can activate the body of the user more appropriately by controller 17 calculating the second irradiation time.

As described above, light-irradiating apparatus 1 according to the present embodiment further includes first light-emitting module 9 and second light-emitting module 10, casing 3 which houses first light-emitting module 9 and second light-emitting module 10, and light-transmissive plate 13 which covers opening 31 formed in casing 3. First light-emitting module 9 and second light-emitting module 10 are approximately orthogonal to opening 31, and disposed in casing 3 such that first light-emitting module 9 and second light-emitting module 10 emit light toward each other.

According to this, compared with the case where white light sources 91 and blue light sources 92 are uniformly disposed on rear portion 32 of casing 3 such that optical axes J of white light sources 91 and blue light sources 92 extend in the positive direction of the X axis, according to the configuration of light-irradiating apparatus 1 according to the present embodiment, the number of blue light sources 92 and the number of white light sources 91 can be reduced by disposing first light-emitting module 9 and second light-emitting module 10 such that first light-emitting module 9 and second light-emitting module 10 face each other. As shown by light-irradiating apparatus 1 according to the present embodiment, light-irradiating apparatus 1 can emit blue light and white light even if first light-emitting module 9 and second light-emitting module 10 are disposed facing each other. Accordingly, an increase in the cost of light-irradiating apparatus 1 due to an increase in the number of components can be prevented with light-irradiating apparatus 1.

Note that it is generally known that exposure to light which includes blue light for a predetermined time period or longer is effective in improving a biological rhythm. In addition, it is generally known that exposure to light which includes white light for a predetermined time or longer is effective in activating brain waves. Accordingly, light-irradiating apparatus 1 can activate the body by emitting light having a predetermined wavelength and a predetermined brightness toward eyes.

As described above, light-irradiating apparatus 1 according to the present embodiment includes blue light sources 92. First light-emitting module 9 includes white light sources 91 and first blue light sources 92 among blue light sources 92, and second light-emitting module 10 includes second blue light sources 92 among blue light sources 92. First blue light sources 92 included in first light-emitting module 9 are disposed closer to rear portion 32 of casing 3 than white light sources 91, rear portion 32 being opposite opening 31.

According to this, white light sources 91 of first light-emitting module 9 are located on the opening side, and blue light sources 92 of second light-emitting module 10 are located on the opening side, and thus emitted light on one side appears white, and emitted light on the other side appears blue. Stated differently, the color gradually changes from white to blue like gradations from one side of light-transmissive plate 13 to the other side thereof (in the present embodiment, from the negative side of the Z axis to the positive side of the Z axis). Light-irradiating apparatus 1 having such a configuration emits light that looks like a blue sky, and thus a user feels comfortable.

As described above, light-irradiating apparatus 1 according to the present embodiment emits light which gradually changes from blue to white from one side of light-irradiating apparatus 1 to the other side of light-irradiating apparatus 1.

As described above, light-irradiating apparatus 1 according to the present embodiment includes casing 3 which houses white light sources 91 and blue light sources 92, and light-transmissive plate 13 which covers opening 31 formed in casing 3. White light sources 91 and blue light sources 92 are disposed on the rear portion of casing 3 which is opposite opening 31 such that white light sources 91 and blue light sources 92 emit light toward opening 31.

As described above, light-irradiating apparatus 1 according to the present embodiment emits light having a luminance which gradually decreases from one side of light-irradiating apparatus 1 to the other side of light-irradiating apparatus 1.

As described above, in light-irradiating apparatus 1 according to the present embodiment, white light sources 91 emit light having a color temperature in a range from 2000 K to 8000 K.

As described above, in light-irradiating apparatus 1 according to the present embodiment, controller 17 is one of a microcomputer, a processor, and a dedicated circuit.

As described above, in light-irradiating apparatus 1 according to the present embodiment, the biological effect threshold is calculated by multiplying a predetermined coefficient by an irradiance, and the biological effect threshold is multiplied by the second irradiation time to calculate an irradiation time for activating the body.

Other Variations Etc.

The above completes description of the light-emitting apparatus according to the present disclosure based on the embodiments, yet the present disclosure is not limited to the above embodiments.

For example, in the above embodiment, a light-irradiating apparatus is used as an example of a light-emitting apparatus, but the light-emitting apparatus is not limited to a light-irradiating apparatus, and may be an illumination apparatus, for example. In this case, if the illumination apparatus emits strongly bluish light, objects including people and equipment appear bluish in, for example, the office environment, and thus a user is likely to feel odd. Accordingly, if the duty cycle of the blue light sources is controlled and set to 75% or less, odd feeling that a user has is reduced, compared to the case where the duty cycle of the blue light sources is 100%.

In the above embodiment, the shape of the light-irradiating apparatus is rectangular, but may not be rectangular in a plan view of the light-irradiating apparatus (when viewed from the positive side of the X axis). For example, the light-irradiating apparatus may have a circular shape, a polygonal shape such as a triangular shape, or a semicircular shape, for instance, or may have a shape which is a combination of such shapes. For example, if the light-irradiating apparatus has a circular shape, a light-emitting module may be uniformly disposed on the inner circumferential surface of the casing, or the first light-emitting module and the second light-emitting module may be disposed in point symmetry relative to the center of the circle. In other words, the first light-emitting module and the second light-emitting module which are arc-shaped may be disposed symmetrically.

In the above embodiment, a plurality of light sources may be uniformly disposed on a rear portion of the casing such that the optical axes of the plurality of light sources extend in the positive direction of the X axis. For example, the light sources may be disposed on the rear portion of the casing in a houndstooth check or in a checkered pattern, for instance. Blue light sources and white light sources may be alternately disposed in units of one or more or a line of blue light sources and a line of white light sources may be alternately disposed. A plurality of white light sources may be disposed in a line, and blue light sources may be disposed on both sides of the line of the white light sources.

In the above embodiment, only blue light sources may be turned on, and only white light sources may be turned on. User operation may additionally turn on white light sources while only blue light sources are on and vice versa. Furthermore, user operation may turn off blue light sources that are emitting light, and turn on white light sources that are emitting no light, and vice versa (switch between on and off of blue light sources and white light sources).

In the above embodiment, white light sources may be controlled so that the white light sources repeats on and off by performing PWM dimming also on the white light sources. In this case, the on state and the off state of the white light sources are synchronized with the on state and the off state of the blue light sources.

In the above embodiment, a gradation region where the luminance changes gradually may be provided in the case where only white light sources or blue light sources are on. In other words, also when light has a single color, a gradation region may be provided by giving a difference in luminance.

In the above embodiment, the operation unit is electrically connected with the light-irradiating apparatus, yet the light-irradiating apparatus may be operated using a remote control which establishes wireless communication (operation of turning on and off a power supply, for instance). The wireless communication is achieved by providing the light-irradiating apparatus with a communication unit which wirelessly communications with the remote control. The communication unit is an apparatus having a close-proximity wireless communication, such as, for example, ZigBee (registered trademark), Wi-Fi (registered trademark), and Bluetooth (registered trademark).

In the above embodiment, a chip on board (COB) module on which an LED chip is directly mounted on a wiring substrate may be used for a light source. A light emitting element included in a light source is not limited to an LED and, for example, may be another solid light emitting element such as a semiconductor light emitting element such as a semiconductor laser, or an electro luminescent (EL) element such as an organic EL element or an inorganic EL element.

The present disclosure may also include embodiments as a result of various modifications that may be conceived by those skilled in the art to the above embodiment, and embodiments obtained by combining elements and functions in the above embodiment in any manner without departing from the spirit of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A light-emitting apparatus which emits light for activating a body, the light-emitting apparatus comprising:
a blue light source;
a white light source; and
a controller which controls the white light source and the blue light source and which adjusts an irradiation intensity of light emitted by the blue light source and an irradiation intensity of light emitted by the white light source, wherein
the controller causes the white light source to continuously maintain an on state and causes the blue light source to repeat an on state and an off state,
the controller causes a sum of the irradiation intensity of the light which is emitted by the white light source and the irradiation intensity of the light which is emitted by the blue light source to be greater than or equal to a biological effect threshold at which light produces an effect of activating the body, and
the controller divides a duty cycle of the blue light source by a first irradiation time for activating the body to calculate a second irradiation time, and causes the blue light source and the white light source to emit light for the second irradiation time by controlling the blue light source and the white light source.

2. The light-emitting apparatus according to claim 1, wherein
the duty cycle of the blue light source in the on state among the on state and the off state is in a range from 20% to 75%.

3. The light-emitting apparatus according to claim 1, wherein
a frequency at which the blue light source repeats the on state and the off state is greater than or equal to 500 Hz.

4. The light-emitting apparatus according to claim 1, wherein
a sum of an average luminance of the light which is emitted by the blue light source at a light emission surface of the blue light source and an average luminance of the light which is emitted by the white light source at a light emission surface of the white light source is less than or equal to a predetermined luminance.

5. The light-emitting apparatus according to claim 1, wherein
the light emitted by the light-emitting apparatus has a brightness greater than or equal to 750 lx.

6. The light-emitting apparatus according to claim 5, wherein
the light emitted by the light-emitting apparatus has a brightness greater than or equal to 1500 lx.

7. The light-emitting apparatus according to claim 1, further comprising:
a casing which houses the white light source and the blue light source, and which includes an opening; and a light-transmissive plate which covers the opening in the casing, wherein
the white light source and the blue light source are disposed on a rear portion of the casing which is opposite the opening such that the white light source and the blue light source emit light toward the opening.

8. The light-emitting apparatus according to claim 7, wherein
the light emitted by the light-emitting apparatus gradually changes from blue to white from one side of the light-emitting apparatus to another side of the light-emitting apparatus.

9. The light-emitting apparatus according to claim 1, wherein
the light emitted by the light-emitting apparatus has a luminance which gradually decreases from one side of the light-emitting apparatus to another side of the light-emitting apparatus.

10. The light-emitting apparatus according to claim 1, wherein
the light emitted by the white light source has a color temperature in a range from 2000 K to 8000 K.

11. The light-emitting apparatus according to claim 1, wherein
the controller is one of a microcomputer, a processor, and a dedicated circuit.

12. The light-emitting apparatus according to claim 1, wherein
the biological effect threshold is calculated by multiplying a predetermined coefficient by an irradiance, and
the biological effect threshold is multiplied by the second irradiation time to calculate an irradiation time for activating the body.

13. A light-emitting apparatus which emits light for activating a body, the light-emitting apparatus comprising:
a blue light source;
a white light source;
a controller which controls the white light source and the blue light source and which adjusts an irradiation intensity of light emitted by the blue light source and an irradiation intensity of light emitted by the white light source, wherein
the controller causes the white light source to continuously maintain an on state and causes the blue light source to repeat an on state and an off state,
the controller causes a sum of the irradiation intensity of the light which is emitted by the white light source and the irradiation intensity of the light which is emitted by the blue light source to be greater than or equal to a biological effect threshold at which light produces an effect of activating the body;
a first light-emitting module;
a second light-emitting module;
a casing which houses the first light-emitting module and the second light-emitting module, and which includes an opening; and
a light-transmissive plate which covers the opening in the casing, wherein
the first light-emitting module and the second light-emitting module are approximately orthogonal to the opening, and disposed in the casing such that the first light-emitting module and the second light-emitting module emit light toward each other.

14. The light-emitting apparatus according to claim 13, further comprising:
a plurality of the blue light sources including first and second blue light sources, wherein
the first light-emitting module includes the white light source and the first blue light source among the plurality of the blue light,
the second light-emitting module includes the second blue light source among the plurality of the blue light sources, and
the first blue light source included in the first light-emitting module is disposed closer to a rear portion of the casing than the white light source, the rear portion being opposite the opening.

15. The light-emitting apparatus according to claim 14, wherein
the light emitted by the light-emitting apparatus gradually changes from blue to white from one side of the light-emitting apparatus to another side of the light-emitting apparatus.

* * * * *